(12) United States Patent
Mathison

(10) Patent No.: US 7,482,158 B2
(45) Date of Patent: Jan. 27, 2009

(54) COMPOSITE POLYNUCLEIC ACID THERAPEUTICS

(76) Inventor: Brian H. Mathison, 7272 Fordham Pl., Goleta, CA (US) 93117

( * ) Notice: Subject to any disclaimer, the term of this patent is extended or adjusted under 35 U.S.C. 154(b) by 0 days.

(21) Appl. No.: 11/173,061

(22) Filed: Jun. 30, 2005

(65) Prior Publication Data

US 2006/0166916 A1 Jul. 27, 2006

Related U.S. Application Data

(60) Provisional application No. 60/585,284, filed on Jul. 1, 2004, provisional application No. 60/653,682, filed on Feb. 16, 2005.

(51) Int. Cl.
*C12N 5/00* (2006.01)
*C12N 5/02* (2006.01)
*C07H 21/02* (2006.01)
*C07H 21/04* (2006.01)

(52) U.S. Cl. ..................................... 435/375; 536/23.1
(58) Field of Classification Search ................. 435/375; 536/23.1
See application file for complete search history.

(56) References Cited

U.S. PATENT DOCUMENTS

| | | | |
|---|---|---|---|
| 5,503,975 | A | 4/1996 | Smith et al. |
| 5,683,985 | A | 11/1997 | Chu et al. |
| 5,807,746 | A | 9/1998 | Lin et al. |
| 5,922,687 | A | 7/1999 | Mann et al. |
| 6,015,892 | A | 1/2000 | Bennett et al. |
| 6,034,234 | A | 3/2000 | Matsu et al. |
| 6,054,299 | A | 4/2000 | Conrad |
| 6,060,310 | A | 5/2000 | Cho-Chung |
| 6,207,646 | B1 | 3/2001 | Krieg et al. |
| 6,262,033 | B1 | 7/2001 | Morishita et al. |
| 6,268,137 | B1 | 7/2001 | Szyf et al. |
| 6,395,550 | B1 | 5/2002 | Mann et al. |
| 6,774,118 | B1 | 8/2004 | Dzau et al. |
| 6,780,843 | B2 | 8/2004 | Lin et al. |
| 2002/0052333 | A1 | 5/2002 | Dzau et al. |
| 2002/0098162 | A1 | 7/2002 | Morishita et al. |
| 2003/0022870 | A1 | 1/2003 | Dzau et al. |
| 2003/0082800 | A1 | 5/2003 | Conrad et al. |
| 2003/0158143 | A1 | 8/2003 | Gleave et al. |
| 2003/0186922 | A1 | 10/2003 | Dzau et al. |
| 2004/0109843 | A1 | 6/2004 | Morishita et al. |
| 2004/0191779 | A1 | 9/2004 | Zhang et al. |
| 2004/0248837 | A1 | 12/2004 | Raz et al. |
| 2005/0037494 | A1 | 2/2005 | Hecker et al. |
| 2005/0064407 | A1 | 3/2005 | Sun et al. |
| 2005/0119470 | A1 | 6/2005 | Manoharan et al. |
| 2005/0124572 | A1 | 6/2005 | Freier et al. |

FOREIGN PATENT DOCUMENTS

| | | |
|---|---|---|
| WO | WO 92/18522 | 10/1992 |
| WO | WO 98/23782 | 6/1998 |
| WO | WO 98/29430 | 9/1998 |
| WO | WO 99/26634 | 6/1999 |
| WO | WO 99/50455 | 10/1999 |
| WO | WO 00/06589 | 2/2000 |
| WO | WO 00/44774 | 3/2000 |
| WO | WO 00/12695 | 9/2000 |
| WO | WO 00/70092 | 11/2000 |
| WO | WO 00/74742 | 12/2000 |
| WO | WO 01/00647 | 1/2001 |
| WO | WO 01/88124 | 11/2001 |
| WO | WO 02/057480 | 7/2002 |
| WO | WO 02/066071 | 8/2002 |
| WO | WO 03/000724 | 3/2003 |
| WO | WO 03/031459 | 4/2003 |
| WO | WO 03/063911 | 8/2003 |
| WO | WO 03/091432 | 11/2003 |
| WO | WO 03/099339 | 12/2003 |
| WO | WO 2004/026342 | 4/2004 |
| WO | WO 2004/076668 | 9/2004 |
| WO | WO 2004/101816 | 11/2004 |
| WO | WO 2005/004913 | 1/2005 |
| WO | WO 2005/027830 | 3/2005 |
| WO | WO 2005/032455 | 4/2005 |
| WO | WO 2005/035547 | 4/2005 |
| WO | WO 2005/039645 | 6/2005 |
| WO | WO 2005/052121 | 6/2005 |
| WO | WO 2005/056020 | 6/2005 |
| WO | WO 2005/056795 | 6/2005 |
| WO | WO 2005/049106 | 7/2005 |
| WO | WO 2005/111238 | 11/2005 |

OTHER PUBLICATIONS

Garmbari, New trends in the development of transcription factor decoy (TFD) pharmacotherapy. Curr Drug Targets. 5(5): 419-30, 2004.*
Morishita, Molecular therapy to inhibit NFkappaB activation by transcription factor decoy oligonucleotides. Curr Opin Pharmacol. 4(2): 139-46, 2004.*
Miller and Vile, Targeted vectors for gene therapy, FASEB J. 9(2): 190-9, 1995.*
Deonarain, Ligand-targeted receptor-mediated vectors for gene delivery, Exp. Opin. Ther. Patents 8(1): 53-69, 1998; Ashley Publications Ltd. ISSN 1354-3776.*
Verma and Somia, Gene therapy—promises, problems and prospects, Nature 389: 239-42, 1997.*
Crystal, Transfer of genes to humans: early lessons and obstacles to success, Science 270: 404-10, 1995.*

(Continued)

*Primary Examiner*—Thaian N Ton
*Assistant Examiner*—Wu-Cheng W Shen
(74) *Attorney, Agent, or Firm*—David P. Dalke; O'Melveny & Myers LLP

(57) ABSTRACT

Compositions comprising therapeutic polynucleic acids and methods of use. The compositions comprise one or more polynucleic acids sequences having two or more features useful for treating diseases associated with cellular proliferation or growth.

3 Claims, 4 Drawing Sheets

OTHER PUBLICATIONS

Pouton and Seymour, Key issues in non-viral gene delivery, Adv Drug Deliv Rev. 46(1-3): 187-203, 2001.*

Read et al., Barriers to gene delivery using synthetic vectors, Adv Genet. 53: 19-46, 2005.*

Dobson, Gene therapy progress and prospects: magnetic nonoparticle-based gene delivery. Gene Ther. 13(4): 283-7, 2006.*

Johnson-Saliba et al. Gene therapy: optimizing DNA delivery to the nucleus. Curr Drug Targets. 2(4): 371-99, 2001.*

Shoji et al., Current status of delivery systems to improve target efficacy of oligonucleotides. Current Pharmaceutical Design 10(7):785-96, 2004.*

Younes et al., Labelled oligonucleotides as radiopharmaceuticals: pitfalls, problems and perspectives. Curr Pharm Des. 8(16): 1451-66, 2002.*

Gao et al. A single decoy oligodeoxynucleotides targeting multiple oncoproteins produces strong anticancer effects, Mol Pharmacol. 70(5):1621-9, 2006.*

Arteaga, C., (2003) Molecular therapeutics: is one promiscuous drug against multiple targets better than combinations of the molecule-specific drugs? Clin. Cancer res. 9, 1231-1232 (PMID: 12684387).

Bielinska, A. et al., (1990) Regulation of gene expression with double-stranded phosphorothioate oligonucleotides. Science 250, 997-1000 (PMID: 2237444).

Hermeking, H., (2003) The MYC oncogene as a cancer drug target. Curr. Cancer Drug Targets. 3, 163-175 (PMID: 12769686).

Keepers, Y. et al., (1991) Comparison of the sulforhodamine B protein and tetrazollum (MTT) assays for in vitro chemosensitivity testing. Eur. J. Cancer 27, 897-900 (PMID: 1834124).

Li, G-Z et al., (2003) Evidence that exposure of the telomere 3' overhang sequence induces senescence. PNAS, vol. 100, No. 2, 527-531.

Li, G-Z et al., (2004) Signaling pathway requirements for Induction of senescence by telomere homolog oligonucleotides. Experimental Cell Research 301, 189-200 (PMID: 12515865).

Mann, M. et al., (2000) Therapeutic applications of transcription factor decoy oligonucleotides. The Journal of Clinical Investigation, vol. 106, No. 9, 1071-1075.

Miyake, T. et al, (2006) Prevention of abdominal aortic aneurysms by simultaneous inhibition of NFkB and ets using chimeric decoy oligonucleotides in a rabbit model. Gene Therapy 13, 695-704.

Monks, A. et al., (1997) The NCI anti-cancer drug screen; a smart screen to identify effectors of novel targets. Anticancer Drug Des. 12 533-541 (PMID: 9365500).

Morishita, R., (2003) Transcription factor as molecular targets: is transcription factor decoy a novel drug? Curr. Drug Targets. 4, 2 p before 599 (PMID: 14577647).

Reedy, T. et al, (2005) Assessing transcription factor motif draft from noisy decoy sequences. Genome Informatics 16(1): 59-67.

Rhodes, Dr. et al., (2005) Mining for regulatory programs in the cancer transcriptome. Nat. Genet. 37, 579-583 (PMID: 15920519).

Rubinstein, L. et al., (1990) Comparison of in vitro anticancer-drug-screening data generated with a tetrazolium assay. J.Natl.Cancer Inst. 82, 1113-1118 (PMID: 2359137).

SZYF, M. (2001) The role of DNA methyltransferase 1 in growth control. Front Biosci. 6, D599-D609) (PMID: 11282571).

Virag, L. et al., (2002) The therapeutic potential of poly(ADP-ribose) polymerase inhibitors. Pharmacol. Rev. 54, 375-429 (PMID: 12223530).

* cited by examiner

Combination A + B + C
[simple]

Composite A or B or C
[competitive interference]

COMPOSITE POLYNUCLEIC ACID THERAPEUTICS

CROSS-REFERENCE TO RELATED APPLICATIONS

This application claims the benefit of U.S. provisional patent application Ser. No. 60/585,284 filed 1 Jul. 2004, U.S. provisional patent application Ser. No. 60/653,682 filed 16 Feb. 2005 each of which is hereby incorporated in its entirety as if fully set forth.

FIELD OF INVENTION

The present invention relates to compositions comprising therapeutic polynucleic acids and methods of use thereof. In a particular aspect, the invention relates to one or more polynucleic acid sequences possessing two or more features with utility in the treatment of diseases associated with cellular proliferation or growth.

BACKGROUND OF THE INVENTION

A major focus of pharmaceutical research has concentrated on developing molecular entities to regulate gene expression. It is believed that modulation of specific genes will alter or circumvent molecular mechanisms underlying acute and chronic disease.

Many approved antineoplastic agents demonstrate significant adverse effects. Newer therapies seek to avoid non-specific toxicities by selectively targeting cell and disease-specific pathways associated with growth, senescence and cellular transformation.

Highly proliferating cells and groups thereof are often the product of multiple events. With time and unchecked by normal processes maintaining homeostasis, proliferating cells expand in number where some may become genetically unstable and diverse. With continued growth, probabilities increase that cells within these groups acquire and express traits enabling escape from or adaptation to therapy. These cells and groups thereof with time will not possess a single target or Achilles' heel through which a mono-functional entity or "magic bullet" could achieve complete therapeutic success. When complex intracellular networks, crosstalk and cellular redundancies that maintain hyperproliferative states are considered, the discovery and development of mono-functional agents may not represent the best or only therapeutic option.

Polynucleic acid-based structures when designed to mimic and interact with two or more cellular features will be effective therapeutic agents. Reflecting on progress and development of antineoplastic therapeutics over the past decades, there remains a need in the art for multifunctional therapeutics. The characterization and design of such structures is provided herein with evidence that these agents are of enhanced utility.

Factors Modulating Genetic Expression

Decoys in context of the invention are polynucleic acid mimetics capable of diverting transcription factors and other proteins from endogenous targets to modulate expression and alter cellular biochemistry. Mimicry is essential to decoys, where cellular aspects, elements or features are resembled, copied closely or imitated accurately.

Nucleic acid structures functioning as transcription factor decoys have been described by Chu and Orgel in U.S. Pat. No. 5,683,985. In this fashion, transcription factors are attractive targets for therapeutic intervention (Mann, M J, et al., 2000, J. Clin. Invest 106, 1071-1075; Morishita, R2003, Curr. Drug Targets. 4, 2-). Bielinska and coworkers described the use of such decoys as tools to alter transcription activity in vitro (Bielinska, A, et al., 1990, Science 250, 997-1000).

Transcription factor decoys show promise in the treatment of neoplastic disease. U.S. Pat. No. 6,060,310 describes CRE-elements with utility in models of tumor cell growth in vitro and in xenograft models. E2F-elements in U.S. Pat. No. 6,774,118 and US Patent Publication Nos. 20020052333, 20030186922, 20030022870 suggest decoys may have utility in models of cardiovascular disease. However, recent human clinical trial data suggests E2F decoys may not be effective as single agents for some cardiovascular indications. U.S. Pat. No. 6,034,234 describes basic E2F-elements 5'-TTTSSCGS-3' (where S=C or G) that inhibit expression of growth-related genes with broad indications.

GC-rich elements capable of binding SP-factors can act as angiogenesis inhibitors and provide potential therapy in tumor models. Additionally, U.S. Pat. No. 6,262,033 and U.S. Patent Publication Nos. 20020098162 and 20040109843 describe NFKB-elements with utility in diseases associated with cellular proliferation. U.S. Patent Publication No. 20050037494 suggests STAT1 may bind specifically to unique sequences. As constructed and in conjunction with some STAT-elements, ETS-elements may play important roles in angiogenesis, matrix remodeling, and cancer progression.

Decoy approaches to EGR1 will be beneficial as overexpression of EGR1 and target genes have been shown as factors contributing to prostate cell proliferation. Decoys with E-box-elements may also be beneficial as associated with genetic regulation through the binding HIF1A, TFE3, USF1 and other proteins. Of particular importance are MXD1$^{(MAD)}$, and MXI1 as MAX-interacting proteins where deregulation of MYC has been implicated in the development of several human cancers (Hermeking, H2003, Curr. Cancer Drug Targets. 3, 163-175).

Transcription factors and other DNA associating factors as overexpressed in disease states suggest that the use of DNA mimicry will have utility. E-Box-, NFKB-, CRE/ATF- and E2F-related transcription factors are disproportionately overexpressed in specific cancers (Rhodes, D R, et al., 2005, Nat. Genet. 37, 579-583). Particularly attractive towards development of polynucleic acids containing E2F-, SP-, NFKB-, EGR-, E-box-, ETS-, and CRE/ATF-related elements will be activity as angiogenesis inhibitors. Those familiar with current therapeutic strategies for cancers recognize that targeting either active proliferating cells or the neovascularization required for sustaining and facilitating tumor growth as important and desirable characteristics.

Hybridization with cellular polynucleic acids may also be a form of polynucleic acid therapy. 'Antisense agents' represent a class of therapeutics designed to inhibit the expression of genes in a selective and sequence specific manner. U.S. Pat. No. 6,015,892 describes the antineoplastic potential of a number of 20 base pair sequences. Antisense methods for PRKCA continues in clinical trials with specific applications in oncology although single agent trials have been discouraging. This provides additional evidence that composite therapeutics or uses in combination with existing chemotherapy are necessary for clinical utility in humans. RAD51C is one homolog of the RAD-family of proteins that have a role in homologous recombination, DNA repair, and cellular proliferation or growth. Increased sensitivity to radiation can also be achieved by antisense methods and amplification of the chromosomal region 17q22-q24 associated with RAD51C/

RAD51L3$^{(RAD51D)}$ and RPS6KB1 are common findings in breast cancer that may contribute to an aggressive clinical course.

In mammalian genomic DNA, 5-methylcytosine is the only known modified base where DNA methyltransferases and methylated-DNA-binding proteins are thought to play important biological roles in development and pathological processes. DNMTs may be important targets for therapy (Szyf, M2001, Front Biosci. 6, D599-D609). One attractive therapeutic aspect of DNA methyltransferase inhibitors are that they appear to inhibit DNA replication. U.S. Pat. No. 6,268,137 describes specific DNA hairpin inhibitors of DNA methyltransferase that form stable noncovalent complexes in a manner independent of S-adenosylmethionine. U.S. Pat. No. 5,503,975 describes additional self-associating artificial polynucleic acids that included 5-fluorocytosine (5FC) at positions corresponding to methylation sites. 5-methylcytosine and other modified bases as present in specific CpG containing sequences will also have potential to interact with methylated-DNA-binding proteins.

Characterized with polynucleic acid therapies are additional phenomena associated with immune system modulation. This occurs to varying degrees in response to polynucleotides where 5'-CpG-3' pairs are present in specific sequence contexts. While there is a great deal of research in attempting to understand CpG molecular effects, a fair generalization is that these represent innate host defense responses to the presence of foreign DNA that can occur with prokaryotic or viral infections. U.S. Pat. No. 6,207,646 is one of many related patents describing these effects. How CpGs present may or may not show immunomodulatory activity, directly or indirectly in concordance with elements for CRE/ATF-, SP-, EGR-, STAT-, E-box-, ETS-, NFKB-elements is unknown as these responses require many of these transcription factors and associated pathways.

Factors Associated with Genetic Integrity

Specific sequences may interfere with proteins associated with telomere maintenance. Inhibitors may be molecular entities that simply resemble 'telomeres' or otherwise associate with proteins or polynucleic acid components of proteins involved in telomere maintenance. The human telomeric protein POT1 is known to bind single-stranded DNA and may participate as a regulator of telomere length in association with factors such as TERT and TERC. Treatment with polynucleotides homologous to telomere overhangs may induce senescence with benefits in neoplastic disease (Li, G Z, et al., 2004, Exp. Cell Res. 301, 189-200; Li, GZ, et al., 2003, Proc. Natl. Acad. Sci. U.S.A 100, 527-531). However 'T-oligo' treatment alone may not be clinically useful in patients with late stage melanomas again suggesting mono-functional therapies may not be the best clinical approach.

Structures that mimic DNA damage such as gaps, nicks, breaks, or that use non-standard bases and spacers may inhibit cellular growth through multiple pathways associated with DNA repair and genetic integrity that can trigger cellular senescence (e.g., programmed cell death or apoptosis). DNA damage is known to activate checkpoint pathways and halt cell cycle progression. For example, 9-1-1 complexes can be associated with early checkpoint signaling, whereas CDC25A, ATR, CHEK1, and polymerases such as POLB are important for cell cycle progression. DEK may bind more complex polynucleic acid structures independent of sequence. Chromatin-associated poly(ADP-ribose) polymerases (PARPs) may also increase cellular sensitivity to DNA-damaging agents, topoisomerases, and ionizing radiation (Virag, L, et al., 2002, Pharmacol. Rev. 54, 375-429).

Overall, composite agents integrating two or more features inhibiting cellular growth by interfering with genetic expression and triggering pathways related to programmed cell death is intended to create therapeutics of greater efficacy.

Although combinations of polynucleic acid therapies with other small molecules are well known, inter- and intra-associating polynucleic acids integrating two or more features for therapeutic benefit are unrealized or less common. U.S. Patent Publication No. 20040109843 describes the use of a single polynucleic acid targeting NFKB- and ETS-related factors. However, the current invention employs several additional factors without use of intervening sequences. Furthermore, the current invention positions described elements deliberately to impart competitive aspects to binding. Considering the juxtaposition of auxiliary elements, binding of factors as associated with the regulation of genetic expression can be considered 'either A or B' not 'A and B' characteristic of simple combinations.

The use of a single polynucleic acid sequence complementary to two cellular mRNAs acting as a 'bispecific antisense agent' is known. U.S. Patent Publication No. 20030158143 describes the administration of such a bispecific antisense oligonucleotide in amounts effective to reduce IGFBP-2 and/or IGFBP-5 in cells associated with endocrine-regulated tumor cells. Additional bispecific agents are known, however use of one, two or more base or nucleobase sequences that in single stranded form may inhibit cellular growth through complementary hybridization to mRNAs via antisense mechanisms (i.e., PRKCA and RAD51C), that in combination or when used with appropriate complement sequences forms duplexes containing two or more binding sequences for two or more transcription factors is unknown.

Additional multifunctional approaches using polynucleic acid based therapeutics are known. U.S. Patent Publication No. 20050064407 describes a DNAzyme that specifically cleaves up to seven BCL2-related mRNA transcripts with potential utility in the treatment of tumors. This is related to the current invention as an example or therapeutic approach using a multitasking or promiscuous agent (Arteaga, CL2003, Clin. Cancer Res. 9, 1231-1232).

The invention can be further distinguished from prior art in numerous ways. Use of polynucleic acids designed to contain transcription factor binding sites also containing 3' tailing sequences intended to interact with additional proteins appears unknown. The addition of one or more 3' overhanging sequences to any duplex-forming sequence capable of functioning as two or more transcription factor decoy(s) for the purpose of also targeting, engaging or interacting with DNA repair proteins or proteins associated with telomere maintenance is unknown.

The use of a sequence with decoy functionality containing CpG dinucleotides wherein cytosines are differentially modified or replaced by 5-methylcytosine or other pyrimides known in that art to cause a more potent inhibition of DNA methyltransferases is unknown. U.S. Pat. No. 5,503,975 describes the use of modified bases or nucleobases, however integration of such sequences with additional sequence elements capable of binding two or more transcription factors is unknown. The use of sequences capable of binding and or inhibiting methylated-DNA-binding proteins and or DNA methyltransferases as also integrating overhanging sequences capable of binding proteins associated with telomere maintenance is unknown. Additionally, use of polynucleic acids containing CpG dinucleotide pairs and their modification by methylation or hemimethylation within auxiliary elements as competitively capable of modulating the binding of transcription factors, serving as substrates, inhibitors, or 'decoys' for DNA methyltransferase (DNMT) and or methylated-DNA-binding proteins, and eliciting host innate immune responses to exposure to foreign polynucleic acids is unrealized or unknown.

The use of two or more auxiliary sequences binding transcription factors and combinations thereof as described and selected from the group of CRE/ATF-, E2F-, SP-, NFKB-, STAT-, EGR-, E-Box-elements collectively for the purposes of inhibiting cellular growth is unknown. Understanding polynucleic acid biotransformation and metabolites, use of backbone modifications in auxiliary sequences of a larger composite structures to facilitate differential persistence of such sequences for hybridization-based activities is also unknown.

To conclude, numerous events and biological activities occur upon contacting cells with polynucleic acids. Primary sequence information and structures formed by inter- and intramolecular associations are primary determinates of these biologic activities. Polynucleic acids described herein represent deliberate designs to achieve unrecognized opportunities in combining two or more polynucleic acid elements and modes of action toward enhancements of biologic activity for therapeutic benefit. In particular, this is where a multi-targeted approach will show improved efficacy and provide persistent therapy for diseases associated with cellular growth.

SUMMARY OF THE INVENTION

The present invention provides methods for inhibiting the growth of mammalian cells including the step of contacting the cells with polynucleotides having SEQ. ID NOs. 1-10 individually or in any combination. In one embodiment, the mammalian cells are human.

In another aspect, the present invention provides methods for treating proliferative diseases in mammals including the steps of administering polynucleotides having SEQ. ID NOs. 1-10 individually or in any combination. In one embodiment, the mammal is a human; in alternate embodiments, the proliferative diseases may be cancer, vascular disease, inflammation, or hyperproliferative disease in any combination. Cancers that are contemplated for treatment according to the present invention include breast, prostate and lung cancer.

In yet another aspect, the present invention provides a composition useful for treating a disease associated with the proliferation of mammalian cells. In one embodiment, the composition is a polynucleotide having SEQ. ID NOs. 1-10 individually or in any combination. In one embodiment, the polynucleic acid includes at least two auxiliary sequences capable of forming two or more cellular structures that, in turn, affect the control of expression or genetic integrity. In another embodiment, the auxiliary sequences share at least two bases or nucleobases. In yet another embodiment, the cellular structures capable of affecting control of genetic expression are transcription factor binding sites. More specifically, the transcription factor binding sites may be E-box-, EGR-, SP-, NFKB-, E2F-, STAT-, ETS-, and CRE-ATF-related sequences individually or in any combination. In still another embodiment, the cellular structures capable of affecting the control of genetic expression are CpG sites associated with DNA methylation, methylated-DNA binding proteins, and immunologic response. In a further embodiment, the cellular structures associated with proteins maintaining genetic integrity are associated with DNA repair or telomere maintenance.

According to a second aspect of the invention, compositions of the invention are comprised of one or more polynucleic acids designed to associate with and or mimic two or more endogenous cellular structures.

According to a third aspect of invention, competitive aspects of protein binding to DNA sequences and auxiliary sequences the invention will provide therapeutic utility specifically in instances where one or more target proteins are differentially expressed in a disease state.

DETAILED DESCRIPTION OF THE INVENTION

According to the present invention, compositions are polynucleic acid molecules that inter- or intramolecularly associate forming two or more features comprising complexes that modulate the transcription of two or more genes in cells. This is where "features" concern a distinct or outstanding part, quality, or characteristic. Preferably, two or more targeted aspects collectively modulate genetic expression associated with cellular growth.

In the context of this invention, "polynucleic acids" or "polynucleotide" refers to polymers of ribonucleic acid (RNA) or deoxyribonucleic acid (DNA) or mimetic thereof including those composed of naturally-occurring nucleobases, sugars and covalent internucleoside (backbone) linkages including linked polyheterocyclic bases having non-naturally-occurring portions that function similarly.

Compounds in accordance with this invention preferably comprise from about 2 to about 100 bases or nucleobases (i.e. from about 2 to about 100 linked nucleosides). A nucleoside is a base-sugar combination where the base portion of the nucleoside is normally a heterocyclic base; most commonly the base or nucleobase is a purine or pyrimidine.

A polynucleic acid "decoy" or phrase "transcription factor decoy" as used herein refers to polynucleic acid elements that mimic native binding sequences or features where proteins may interact. Most commonly, these are typically two more bases or nucleobases in sequences that compete with, sequester or divert proteins from native targets.

An "antisense agent" is a complementary piece of genetic material (DNA or RNA) that binds to another piece of DNA or RNA by base-pairing, which prevents that DNA/RNA fragment from being used to synthesize new proteins. For example, SEQ. ID NO. 1 as illustrated in FIG. 1 may act as an antisense agent for PRKCA, but as administered with a complement sequence to form a duplex is in one particular aspect a composite transcription factor decoy containing CRE/ATF- and E2F-elements.

Desirably, auxiliary sequences or elements are specific for targeted proteins such that their effect on non-target cells and metabolic processes are minimized. Target cells in general are those in hyperproliferative states expressing cell cycle or target proteins at elevated levels in comparison to quiescent cells. Desirably, decoys contain sufficient nucleotide sequence to bind transcription factors and other proteins. In preferred embodiments, two or more auxiliary sequences are selected from the group and capable of interacting with CRE/ATF-, ETS-, E2F-, SP-, NFKB-, EGR-, E-Box-, or STAT-related transcription factors.

Figure 1:
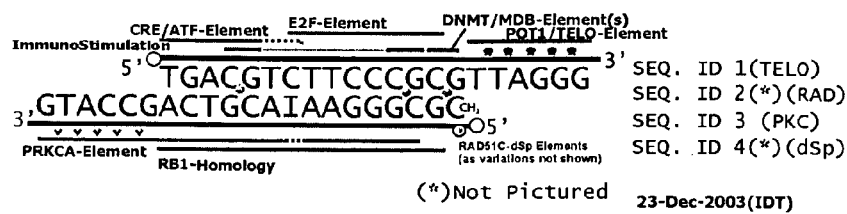
FIG. 1A-1G Schematic illustrations of composite polynucleic acids or prototypes prepared and screened for antineoplastic activity. Sequences are aligned vertically with central box indicating approximate locations of auxiliary sequences known to bind proteins.
Figure 1:
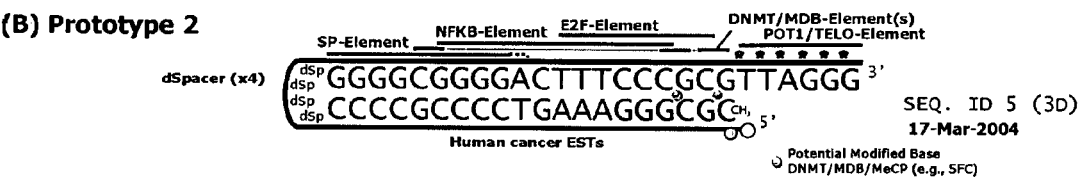
Figure 1:
Figure 1:
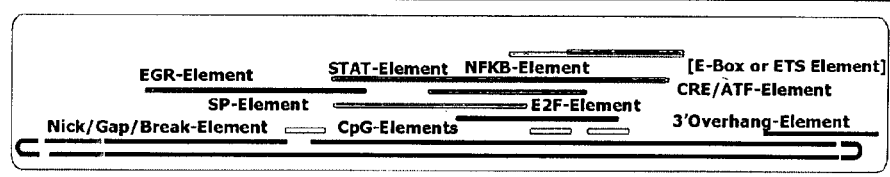
Figure 1:
Figure 1:
Figure 1:

FIG. 1 illustrates aspects of the invention whereby one or more polynucleic acids through intra- or intermolecular association form duplexes linked by one or more intervening sequences, loops, or connectors forming hairpins or dumbbells. These aspects are exemplified by SEQ. ID NOs. 1 or 2 with SEQ. ID NOs. 3 or 4; or SEQ. ID NOs. 5, 6, 7, 8, and 9.

Desirably, additional elements formed through intra- or intermolecular association will possess 5'-CpG-3' pairs or modified bases or nucleobases capable of binding DNA methyltransferases, methylated-DNA-binding proteins, and that are additionally capable of eliciting immunomodulatory effects. Dumbbell structures formed by inter- or intramolecular association creating structures resembling gaps, nicks, breaks and higher order structures such a cruciform are deliberately designed features intended to activate cell cycle checkpoints and DNA repair responses that will contribute to an inhibition of cellular growth. These responses being generally known and associated with pathways of cellular senescence where activation of these pathways are considered a desirable aspects for therapy.

According to additional aspects of the present invention, polynucleic acids may further comprise one or more nucleotide sequences capable of hybridization with cellular RNAs. In preferred embodiments, appropriate spacing or juxtaposition of auxiliary sequences forming two or more decoy elements are designed such that when unassociated or in single stranded form are complementary to endogenous cellular polynucleic acids. Biotransformation products or in single stranded forms, complementary auxiliary sequences will be available for hybridization based activities targeting pathways associated with cellular growth via interactions with mRNAs, protein-RNA complexes, and larger aggregates thereof.

Figure 2:
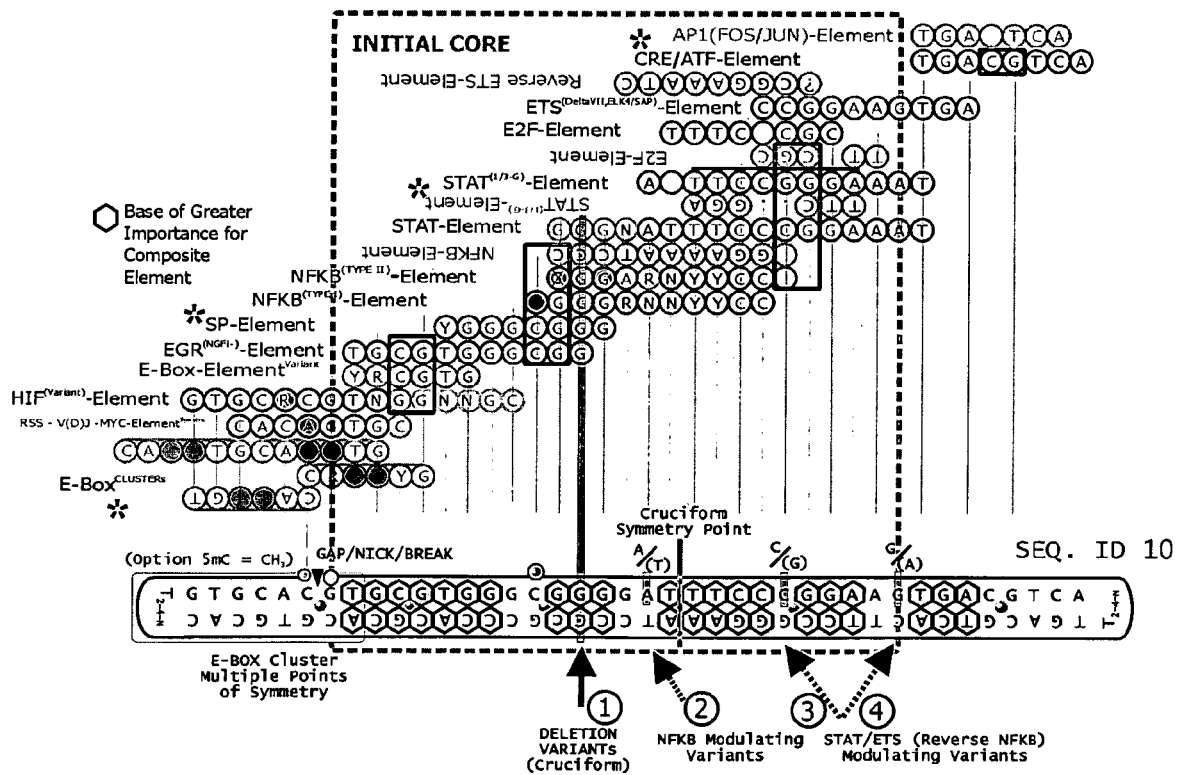
FIG. 2 Schematic illustration of short auxiliary sequences and alignment with transcription factor binding sites shown in relation to one composite polynucleic acid prototype. Dates of sequence preparation are also shown for reference.

FIG. 2 is illustrative of a composite polynucleic acid structure showing auxiliary sequence elements and their juxtaposition. Asterisks (*) indicate short palindrome binding sequences where some E-Box-, STAT-, CRE/ATF-, and to a certain extent SP-related proteins may associate in more than one orientation. Additional non-palindrome elements are shown inverted. CpG pairs are boxed as potential sites of modified bases associated with DNA methylation processes and binding of related proteins. Positions for optional modified bases such as 5-methylcytosine (5mC or m5c) are shown by filled circles adjacent to sequence outline. Additional circles show locations of 5' ends of preferred sequences where it is understood that similar dumbbell structures may be produced by breaks introduced between any two bases or nucleobase pairs of circularizing sequence. Bases or nucleobases within hexagons are considered of greater importance to the formation of composite elements. A cruciform symmetry point is indicated by vertical bar shown centrally within the 5'-AT|TT-3' sequence. Four (4) sites of base or nucleobase variation are indicated as circled 1, 2, 3, and 4. Circle 1, indicates position of a G-deletion variation facilitating formation of a stable cruciform. Circle 2 and 3 indicate potential base pair changes or inversions that are NFKB- (and to a lesser extent STAT- and ETS-) modulating in two orientations. Circle 4 (G->A transversion) is also a comprehended variant capable of modulating the binding of ETS-related factors. SEQ. ID No. 10 is shown as one possible variant. The large dashed box indicates a minimal sequence block capable of significant activity as demonstrated by Prototypes 2, 3, 4a, 4b and 4c as illustrated in FIG. 1.

In a preferred embodiment, invention polynucleic acids will undergo biotransformation yielding additional metabolites that will retain activity to slow cellular growth. Metabolites include shortened polynucleic acids, component phosphothioate nucleotides, thiophosphates, and combinations of any two or more thereof. Polynucleic acids undergo in vivo biotransformation by a variety of systems; however exo- and endonuclease metabolism represents the primary mechanism decreasing effective mass resulting in clearance where the chemical composition and nature of the polynucleic acid backbone are important. Those knowledgeable of polynucleic acid chemistry can imagine chimeras resulting from one or more modifications to nucleic acid structure that will provide resistance to biotransformation. The designed biopersistence of subordinate sequences through backbone modifications as exemplified by SEQ. ID NOs. 1 and 5 are envisioned to enable additional utility to inhibit cellular growth.

Figure 3:
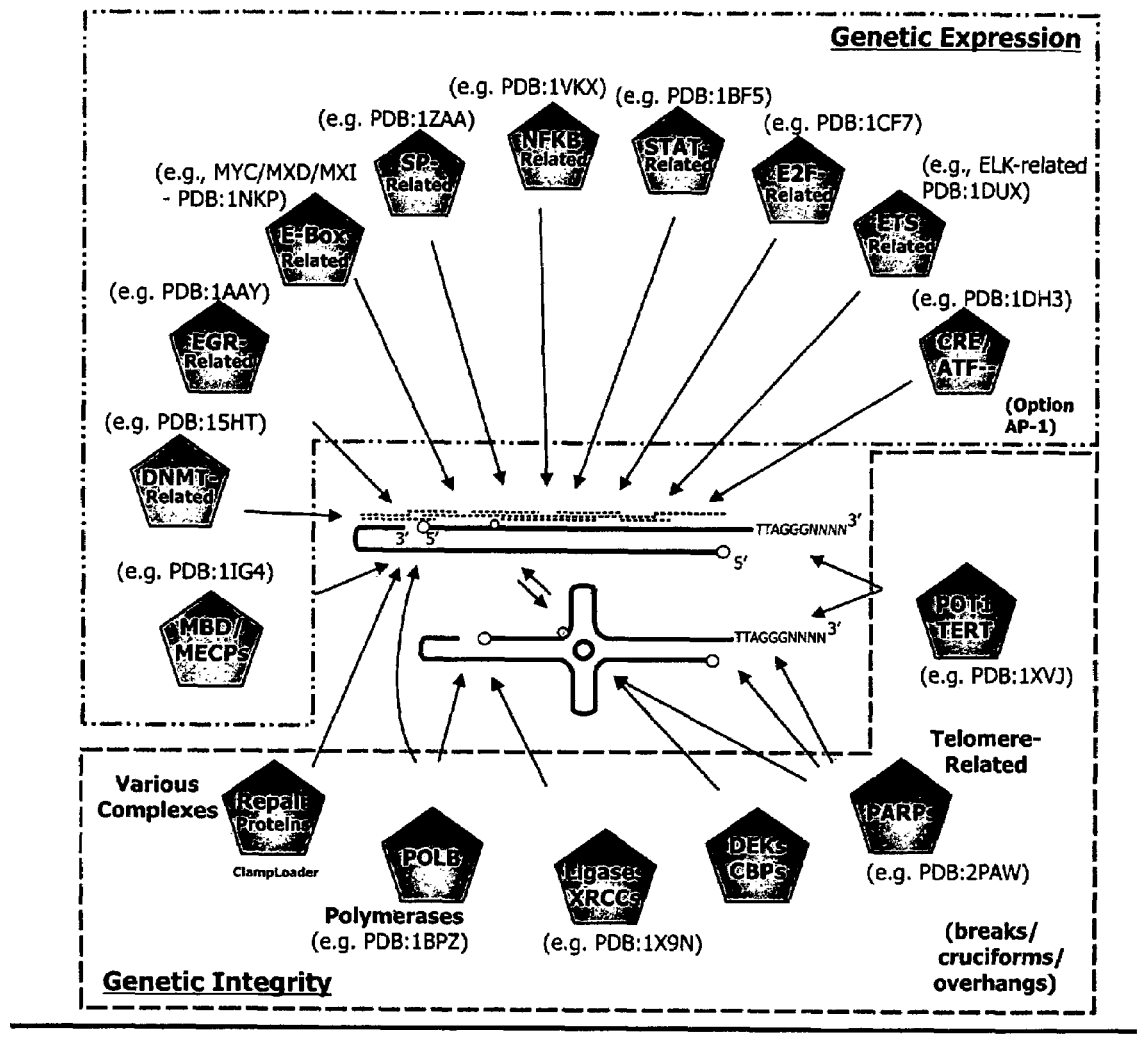
FIG. 3 illustrates potential interactions of a composite polynucleic acid with proteins using representative crystal structures obtained from protein data bank entries. Bottom illustration indicates differences from simple combinations that impart competitive aspects to protein binding.
Figure 3:
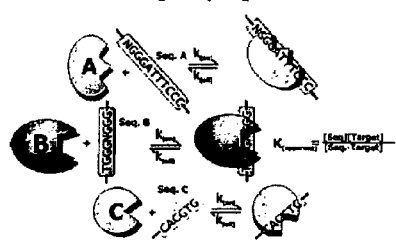
Figure 3:
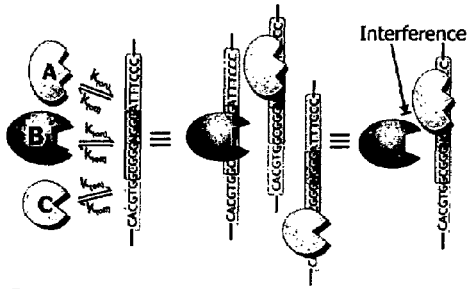

Upon cursory examination, those new to these composite polynucleic acid entities could conclude that the sequences are not significantly different than combinations of the individual elements. Understanding some of the differences and potential utility of these entities involves both element selection and juxtaposition in overlapping or adjacent fashion. FIG. 3 illustrates competitive binding to invention sequences. Representative crystal structures identified by PDB entry code and related to the invention are shown where sizes are depicted and scaled to indicate potential for physical interference. Using invention sequences, targeted factors that are over-expressed will be dampened as a function of concentration and binding avidity. As administered in small amounts, preferred binding will be toward targeted proteins that are over expressed. Similar competitive aspects are known to control expression of native genes.

As therapeutics, composite polynucleic acids will have indications where administration results in sufficient concentrations to slow or prevent cellular growth. Biodistribution of polynucleic acids following intravenous and subcutaneous administration of are known to result in high concentrations in kidney, liver, spleen, lymph, and vascular endothelia. Topical administration may achieve high concentrations in skin. Catheters may allow treatment of bladder epithelia. Inhalation of aerosols or specific formulation(s) may permit delivery to lung and therapeutic treatment of respiratory disease. For example, U.S. Patent Publication No. 20040248837 teaches pulmonary delivery of CpG containing polynucleic acids and is included by reference. Teaching of the intracellular delivery of nucleic acids to specific sites using pressure and devices in known through U.S. Pat. Nos. 5,922,687 and 6,395,550 that are included by reference.

Additional techniques can be used for providing the subject compositions to sites of interest, such as injection, use of catheters, trocars, projectiles, pluronic gel, stents, sustained drug release polymers or other devices that provides for internal access, or the like. Where an organ, tissue, or cell-type is accessible because of removal from the patient, such organ, tissue, or cell may be, bathed or treated in a medium containing the subject compositions. Alternatively, subject compositions may be painted onto the organ or may be applied in any convenient way. In many situations it may be desirable to provide polynucleic acids systemically with additional agents that facilitate favorable biodistribution to target cells and nuclei thereof. This includes but is not limited to conjugation of polynucleic acids with tissue targeting components (e.g., antibodies), peptides (e.g., penetratins or other nuclear localization peptides), polyarginines or polylysines, small molecules (e.g., folates, cholesterols, etc.), and where these agents are incorporated with liposomal delivery systems. U.S. Patent Publication Nos. 20050119470, and 20050124572 teach modifications, modified internucleoside linkages (backbones), modified sugar and internucleoside linkage-mimetics, modified sugars, natural and modified nucleobases, conjugations, chimeric polynucleic acids, formulations, and dosing. These are included by reference.

Use of liposomes and PEI-based systems with or without additional targeting proteins, small molecules and their modifications are contemplated as delivery systems. These and other methods, in the absence inherent pharmacological activity, are regarded as embellishments enhancing the delivery of the active pharmaceutical ingredient to cells and particular sites in a mammal; this is where SEQ. ID NOs. herein are representative of active pharmaceutical ingredients. The above can be contrasted by administration with or conjugation with proteins, peptides or small molecules that possess pharmacologic activities. For example, conjugation of invention with an NFKB peptide may both facilitate delivery and add activity. U.S. Pat. Nos. 6,780,843 and 5,807,746 teach aspects and use of such peptides and are included for reference.

Generation and delivery of polynucleic acids to targeted cells may be achieved by additional vectors. U.S. Pat. No. 6,054,299 and U.S. Patent Publication No. 20030082800 teach stem-loop structures and the use of ssDNA expression vectors for altering gene expression, respectively. These are included by reference in their entirety.

Optimal treatment parameters are generally determined empirically dependent on clinical indication and status. Several routes, formulations, vehicles and methods of administration are envisioned. Treatment may be prophylactic or therapeutic with the subject compositions at frequencies and durations achieving and maintaining pharmacologic activity. Considering auxiliary sequences employed, transcription factors targeted, collections thereof, and their integration, inhibiting cellular growth associated with various cancers, including aspects involving angiogenesis, metastasis, and immunologic response are considered primary therapeutic indications. Treatment of additional conditions associated with cellular growth includes inflammatory disease, particular aspects of cardiovascular disease, particular aspects of macular degeneration and dermatologic disease.

Vascular diseases are inclusive of stenoses that are strictures of any canal commonly applied to narrowing of cardiac structures, vessels and valves. Stenoses may also be applied to pulmonary, and other ductal structures most often associated with an inappropriate growth of cells. Neoplasms or tumors are defined as any swelling or tumefaction or abnormal new mass of tissue that serves no apparent purpose as historically associated with one of the four signs of inflammation (e.g., tumor, calor, dolor, rubor). Inflammation is defined as the fundamental pathologic process consisting of a dynamic complex of cytologic and histologic reactions that occur in blood vessels and adjacent tissues in response to injury that involves cellular growth or stimulation caused by physical, chemical or biologic agents. Hyperproliferative diseases are defined as a mean numerical or quantitative hypertyophy is an increase in the number of cells in a tissue or organ, excluding tumor formation, whereby the bulk of the part or organ is increased. This is contrasted with hypertrophy that should be restricted to denote greater bulk through increase in size, but not number of individual tissue cells. Compositions and methods may be as applied to psoriasis as in alphos, psora and conditions characterized by the eruption of circumscribed, discrete and confluent, reddish silvery-scaled maculopapules. Additionally contemplated are methods applied to warts or verruca, being any growth characterized by circumscribed hypertrophy of the papillae of the corium, with thickening of the malpighian, granular, and keratin layers of the epidermis often associated with viruses, but also inclusive of epidermal verrucous tumors of nonviral etiology.

Sequences of the invention may also be used as diagnostics or as research tools or reagents. U.S. Patent Publication No. 20040191779 teaches some aspects of the analysis of regulatory factor binding sites of differentially expressed genes and is included herein by reference.

While the present invention has been described with specificity in accordance with certain of its preferred embodiments, the following examples serve only to illustrate the invention and are not intended to limit the same.

EXAMPLE 1

Chemistry, Manufacturing and Control. Synthesis and analytical purity determinations for polynucleic acids were performed as is known in the art through the well-known technique of solid phase synthesis. Polynucleic acids were prepared using phosphoramidite chemistry and purified by chromatography. Purification of phosphodiesters and phosphorothioates was conducted using columns to remove low-molecular weight salts and impurities. Integrity and identity information for polynucleic acids used for antineoplastic screening was verified by MALDI TOF and capillary electrophoresis.

EXAMPLE 2

Screens for antineoplastic potential followed procedures similar to those used by the National Cancer Institute Development Therapeutics Program (NCI DTP) (Keepers, Y P, et al., 1991, Eur. J. Cancer 27, 897-900; Monks, A, et al., 1997, Anticancer Drug Des 12, 533-541; Rubinstein, LV, et al., 1990, J. Natl. Cancer Inst. 82, 1113-1118) with exceptions in that transfection enhancers (e.g., Lipofectamine™) were used.

Figure 4:
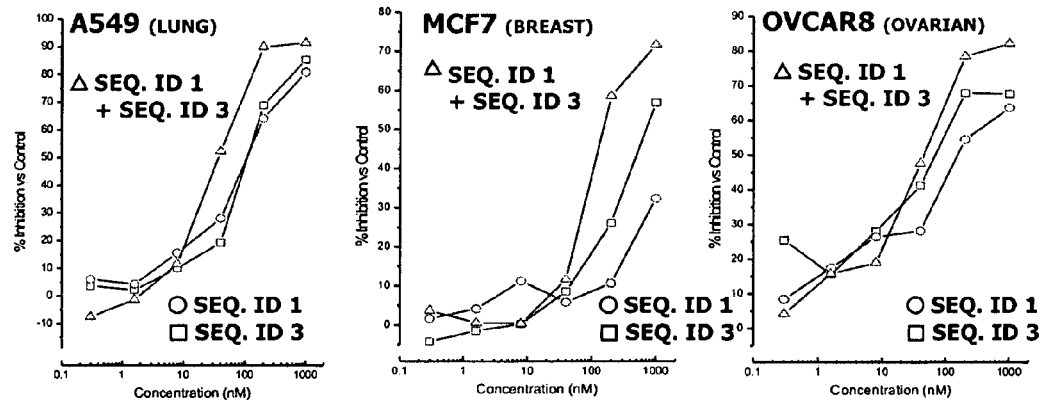
FIG. 4A-4B show tabular and graphic representations of dose-response relationships (percent inhibition of growth versus concentration) following treatment of human cells with invention sequences.
Figure 4:
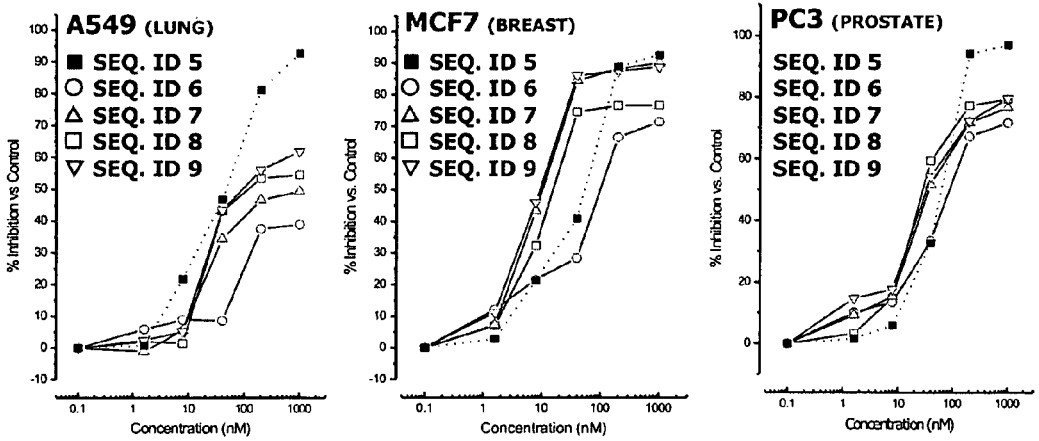

Screening results following treatment of human cancer cells lines A549 (lung); MCF7 (breast); and OVCAR8 (ovarian) treated with SEQ. ID NO. 1 and 3 individually and as combined following a brief annealing step are shown in FIG. 4(A). Both tabular and graphed data demonstrate differences between the single stranded polynucleic acids and the product of association following annealing. Individually, each strand showed activity in inhibiting cell growth with a characteristic dose-response curve. $IC_{50}$ values (concentrations producing half maximal growth) for each of the individual single strand sequences (SEQ. ID NO. 1 and SEQ. ID NO. 3) is shown. These are not unlike those characterized in prior art for antisense agents. However, data for the annealed product of the two strands as forming additional elements for CRE/ATF- and E2F-related factors demonstrates an increased potential to inhibit cellular growth in regards to both maximal inhibitory response [y-axis] and estimated $IC_{50}$ value. In cell lines utilized, individual strands showed concentration-dependent activity, but as annealed showed improvements demonstrating additional and unexpected benefits are obtainable. Those skilled in the art for related technologies would appreciate that $IC_{50}$ values as estimated in the low nanomolar range are equivalent or superior to that of known transcription factor decoys, DNA methyltransferase inhibitors, and antisense agents of similar composition. Those skilled in the art will also recognize that designs of screening studies producing this data under may under represent antineoplastic potential with regards to proteins associated with telomere maintenance as additional cellular divisions would ordinarily be required. This in part supports one explanation for slightly improved responses of the A549 cell line.

Additional screening data obtained for SEQ. ID NOs. 5-9 (Prototypes 2, 3, 4a, 4b, and 4c) are tabulated and graphed in FIG. 4(B). Prototype 2 is a single polynucleic acid forming a hairpin that through intramolecular association also produces a 3'-overhanging sequence as illustrated in FIG. 1. Duplex regions formed result in SP-, NFKB- and E2F-elements. As observed with Prototype 1 results, dose-dependent inhibition of cellular growth was observed in the cell lines assessed. $IC_{50}$ estimates where in the low nanomolar (nM) range for A549 & H226, MCF7 & MDA MB231, and PC3. A weaker response was observed with LnCAP cells where the $IC_{50}$ value was somewhat dissimilar in comparison to other cell lines.

FIG. 4(B) shows dose-response data from separate experiments. Of significance is the assessment of Prototypes 4a, 4b, and 4c where SEQ. ID NO. 8 (Prototype 4b, shown as open circles) was constructed with CpG pairs inverted relative to SEQ. ID NO. 7 (Prototype 4a; open triangle pointed up) and SEQ. ID NO. 9 (Prototype 4c, open triangle pointed down).

Prototype 4c possesses slight modifications to facilitate increased STAT-element binding. Prototype 4b was not as efficacious considering $IC_{50}$ values or maximum inhibitory capabilities. This is important as inversion of CpG pairs would disrupt several auxiliary sequences binding transcription factors with the exception of NFKB- and SP-elements. This data supports that NFKB- and SP-elements contribute significantly to growth inhibition in the cell lines assessed. However the presence of additional elements as identified in schematics adds and increases growth inhibitory activities in both breast and prostate cell lines.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned. The examples provided herein are representative of preferred embodiments, are exemplary, and are not intended as limitations on the scope of the invention. Modification and other uses will occur to those skilled in the art. These modifications are encompassed within the spirit of the invention and are defined by the scope of the claims.

The entire disclosure of each patent, patent application, and publication cited or described in this document is hereby incorporated by reference. The disclosure of all publications cited above, and the disclosure document are expressly incorporated herein by reference, each in its entirety, to the same extend as if each were incorporated by reference individually.

What is claimed is:

1. A method for inhibiting the growth of mammalian cells in vitro, the method comprising the step of contacting mammalian cells with a polynucleic acid consisting of the sequence set forth in SEQ ID NO. 9, wherein said contact results in inhibition of the growth of the mammalian cells.

2. The method of claim 1, wherein the mammalian cells are of human origin.

3. An isolated polynucleic acid consisting of the sequence set forth in SEQ ID NO. 9.

* * * * *

```
                            SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Standard Synthesis
<220> FEATURE:
<221> NAME/KEY: misc_feature
<222> LOCATION: (16)..(21)
<223> OTHER INFORMATION: Phosphorothioate Linkage, Chimeric backbone,
      3'-OH six base pair overhang

<400> SEQUENCE: 1
tgacgtcttc ccgcgttagg g                                          21

<210> SEQ ID NO 2
<211> LENGTH: 21
<212> TYPE: DNA
<213> ORGANISM: Artificial Sequence
<220> FEATURE:
<223> OTHER INFORMATION: Standard Synthesis
<220> FEATURE:
<221> NAME/KEY: misc_feature
<222> LOCATION: (16)..(21)
<223> OTHER INFORMATION: Phosphorothioate Linkage, Chimeric backbone,
      3'-OH six base pair overhang

<400> SEQUENCE: 2
tgacgtcttc ccgcgcatcg c                                          21

<210> SEQ ID NO 3
<211> LENGTH: 21
<212> TYPE: DNA
```

```
<213> ORGANISM: Artificial Sequence
<220> FEATURE:
<223> OTHER INFORMATION: Standard Synthesis
<220> FEATURE:
<221> NAME/KEY: modified_base
<222> LOCATION: (1)..(1)
<223> OTH
      ER INFORMATION: m5c FEATURE:
<221> NAME/KEY: modified_base
<222> LOCATION: (9)..(9)
<223> OTHER INFORMATION: I (deoxyinosine)
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (16)..(21)
<223> OTHER INFORMATION: Phosphorothioate Linkage, Chimeric backbone,
      3'-OH six base pair overhang

<400> SEQUENCE: 3
cgcgggaana cgtcagccat g                                              21

<210> SEQ ID NO 4
<211> LENGTH: 21
<212> TYPE: DNA
<213> ORGANISM: Artificial Sequence
<220> FEATURE:
<223> OTHER INFORMATION: Standard Synthesis
<220> FEATURE:
<221> NAME/KEY: modified_base
<222> LOCATION: (1)..(1)
<223> OTHER INFORMATION: m5c (5-methylcytosine)
<220> FEATURE:
<221> NAME/KEY: modified_base
<222> LOCATION: (9)..(9)
<223> OTHER INFORMATION: dSpacer (abasic site)
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (16)..(21)
<223> OTHER INFORMATION: Phosphorothioate Linkage, 3'-OH six base pair
      overhang

<400> SEQUENCE: 4
cgcgggaana cgtcagccat g                                              21

<210> SEQ ID NO 5
<211> LENGTH: 50
<212> TYPE: DNA
<213> ORGANISM: Artificial Sequence
<220> FEATURE:
<223> OTHER INFORMATION: Standard Synthesis
<220> FEATURE:
<221> NAME/KEY: modified_base
<222> LOCATION: (1)..(1)
<223> OTHER INFORMATION: m5c (5-methylcytosine)
<220> FEATURE:
<221> NAME/KEY: misc_feature
<222> LOCATION: (21)..(24)
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (45)..(50)
<223> OTHER INFORMATION: Phosphorothioate Linkage, Chimeric backbone,
      3'-OH six base pair
      overhang
```

```
<400> SEQUENCE: 5
cgcgggaaag tccccgcccc nnnnggggcg gggactttcc cgcgttaggg          50

<210> SEQ ID NO 6
<211> LENGTH: 52
<212> TYPE: DNA
<213> ORGANISM: Artificial Sequence
<220> FEATURE:
<223> OTHER INFORMATION: Standard Synthesis
<220> FEATURE:
<221> NAME/KEY: misc_feature
<222> LOCATION: (16)..(19)
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (42)..(45)
<220> FEATURE:
<221> NAME/KEY: misc_feature
<222> LOCATION: (42)..(45)
<223> OTHER INFORMATION: n is a, c, g, or t

<400> SEQUENCE: 6
ggggactttc ccgcgnnnnc gcgggaaagt ccccgccccc tnnnnagggg gc       52

<210> SEQ ID NO 7
<211> LENGTH: 72
<212> TYPE: DNA
<213> ORGANISM: Artificial Sequence
<220> FEATURE:
<223> OTHER INFORMATION: Standard Synthesis

<400> SEQUENCE: 7
ttgcgtgggc ggggatttcc cgcacgtgac gtcattttg acgtcacgtg cgggaaatcc  60
ccgcccacgc aa                                                    72

<210> SEQ ID NO 8
<211> LENGTH: 72
<212> TYPE: DNA
<213> ORGANISM: Artificial Sequence
<220> FEATURE:
<223> OTHER INFORMATION: Standard Synthesis

<400> SEQUENCE: 8
ttggctgggg cgggatttcc gccagctgag ctcattttg agctcagctg cggaaatcc   60 cgccccagcc aa                                                    72

<210> SEQ ID NO 9
<211> LENGTH: 72
<212> TYPE: DNA
<213> ORGANISM: Artificial Sequence
<220> FEATURE:
<223> OTHER INFORMATION: Standard Synthesis

<400> SEQUENCE: 9
ttgcgtgggc ggggatttcc cggaaatgac gtcattttg acgtcatttc cgggaaatcc  60
ccgcccacgc aa                                                    72

<210> SEQ ID NO 10
<211> LENGTH: 88
<212> TYPE: DNA
<213> ORGANISM: Artificial Sequence
<220> FEATURE:
<223> OTHER INFORMATION: Standard Synthesis
```

```
<220> FEATURE:
<221> NAME/KEY: misc_feature
<222> LOCATION: (12)..(12)
<223> OTHER INFORMATION: Deletion Option bp 12 with 60
<220> FEATURE:
<221> NAME/KEY: misc_feature
<222> LOCATION: (15)..(15)
<223> OTHER INFORMATION: Base Option A/T being T paired with position 58
      A
<220> FEATURE:
<221> NAME/KEY: misc_feature
<222> LOCATION: (21)..(21)
<223> OTHER INFORMATION: Base Option C/G being G paried with position 52
      C
<220> FEATURE:
<221> NAME/KEY: misc_feature
<222> LOCATION: (26)..(26)
<223> OTHER INFORMATION: Base Option G/A being A paired with position 47
      T
<220> FEATURE:
<221> NAME/KEY: stem_loop
<222> LOCATION: (26)..(26)
<223> OTHER INFORMATION: Thymidine loop
<220> FEATURE:
<221> NAME/KEY: stem_loop
<222> LOCATION: (79)..(82)
<223> OTHER INFORMATION: Thymidine loop

<400> SEQUENCE: 10
gtgcgtgggc ggggatttcc cggaagtgac gtcatttttg acgtcacttc cgggaaatcc    60
ccgcccacgc acgtgcactt ttgtgcac                                      88
```